United States Patent
Wixey et al.

(10) Patent No.: US 6,520,021 B1
(45) Date of Patent: Feb. 18, 2003

(54) PRESSURE MEASURING DEVICE

(75) Inventors: David Wixey, Auckland (NZ); Yann Ren Breton, Paris (FR); Patrick Sean McSweeny, Les Loges (FR)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/619,784

(22) Filed: Jul. 20, 2000

(30) Foreign Application Priority Data

Jul. 28, 1999 (NZ) .................................................. 336948

(51) Int. Cl.⁷ .................................................. G01L 7/00
(52) U.S. Cl. ...................................................... 73/714
(58) Field of Search ................................ 73/168, 865.5, 73/756, 714, 700, 705, 713, 747, 1.57, 1.66, 1.67, 748–750

(56) References Cited

U.S. PATENT DOCUMENTS

| 785,438 A | * | 3/1905 | Sargent | 73/749 |
|---|---|---|---|---|
| 2,295,528 A | * | 9/1942 | Cutter et al. | 73/747 |
| 2,422,702 A | * | 6/1947 | Rodanet | 73/1.66 |
| 2,686,429 A | * | 8/1954 | West | 73/747 |
| 3,817,097 A | * | 6/1974 | Heroux | 73/168 |
| 5,148,712 A | * | 9/1992 | Cross et al. | 73/756 |
| 5,271,278 A | * | 12/1993 | Salgues | 73/700 |

FOREIGN PATENT DOCUMENTS

| FR | 1035315 | * | 8/1953 | 73/700 |
|---|---|---|---|---|
| GB | 23919 | * | of 1900 | 73/756 |

* cited by examiner

*Primary Examiner*—Robert Raevis
(74) *Attorney, Agent, or Firm*—Trexler, Bushnell, Giangiorgi, Blackstone & Marr, Ltd.

(57) ABSTRACT

A connector is formed to connect with the outlet of a humidification chamber. A calibrated tube extends through the connector to be retained in use in at least a substantially vertical direction. A bias flow outlet also extends through the connector. In use the connector of the measuring device is fitted to the outer port of a humidification water chamber with the calibrated tube extending into the reservoir of water within the chamber. With an air supply to the chamber activated the subsequent water level in the tube indicates the operating pressure of the blower under a flow condition simulating losses through leakage in the breathing circuit and at the patient connection.

19 Claims, 2 Drawing Sheets

PRESSURE MEASURING DEVICE

BACKGROUND TO THE INVENTION i) Field of the Invention

This invention relates to pressure measuring devices and in particular to devices suitable for measuring the output characteristics of a CPAP blower.

ii) Summary of the Prior Art

Breathing circuits have been known for some time incorporating in line humidification devices. A common form of humidification device includes a water containing humidification chamber fitted to a heater base. Gases flowing through the humidification chamber are humidified from the heated water reservoir therein. Breathing circuits of this type have been used in artificial or assisted ventilation systems.

More recently such humidification systems have been adopted in CPAP treatment of obstructive sleep apnea. Devices such as the HC200 (available form the applicant) integrate the CPAP blower and the humidifier heater base. The chamber slides onto the heater base and accomplishes simultaneous connection with the outlet of the CPAP blower. A humidification chamber for use with such a machine is depicted in FIG. 3.

For the comfort of the user it is desirable from time to time to check and/or adjust the pressure provide by the CPAP blower.

SUMMARY OF THE INVENTION

It is an object of the present invention to provide a measuring device which goes some way to meeting the above desiderata or which will at least provide users with a useful choice.

In a first aspect the invention consists in a measuring device comprising:

A connector formed to connect with the outlet of a humidification chamber, a calibrated tube extending through said connector to be retained in an at least substantially vertical direction through a said outlet with said connector fitted to the said outlet, and a bias flow outlet through said connector.

In a still further aspect the invention consists in a method of assessing the operation of a CPAP blower comprising:

filling a water chamber to a level, connecting said chamber to said CPAP blower, fitting a connector having an orifice therethrough, a calibrated tube passing through said orifice, and a gases flow bypass of predetermined flow constraint, to the outlet of the water chamber.

adjusting the position of said tube through said connector such that a predetermined point on said tube aligns with the level of said water within said chamber, activating said CPAP blower, waiting for the liquid level in said tube to reach a stable position, and assessing performance of the CPAP blower by comparing the attained level of said water in said tube with a desired level.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

Figure 1:
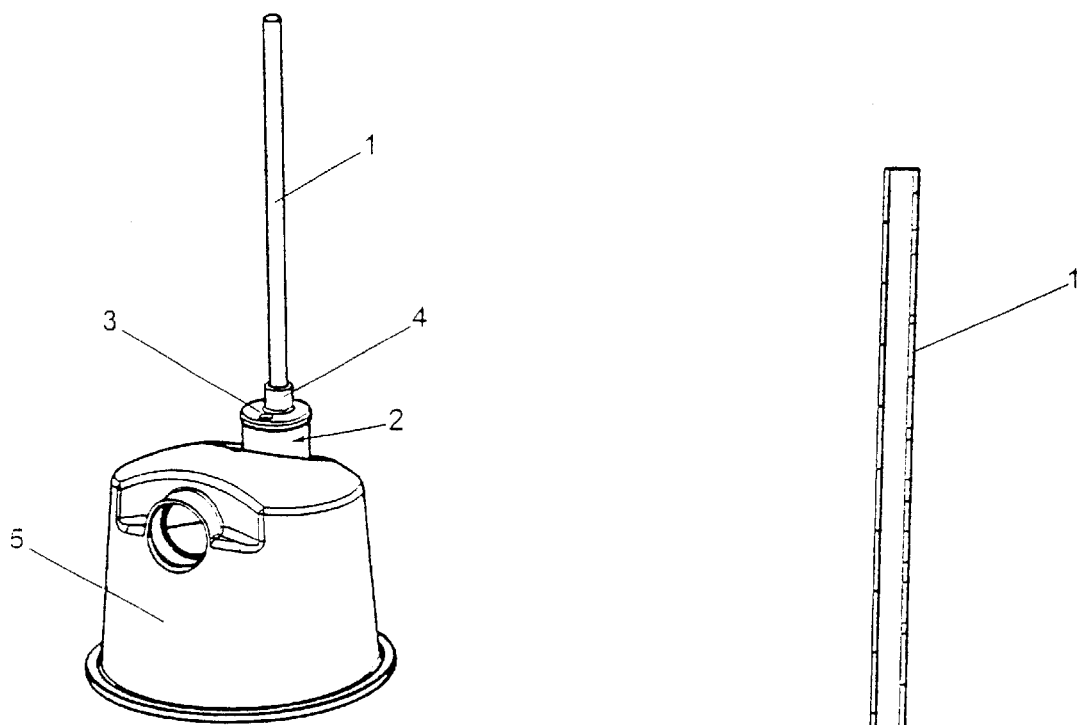
FIG. 1 is a perspective view of a humidifier water chamber incorporating the measuring device according to the present invention connected to the outlet thereof.
Figure 2:
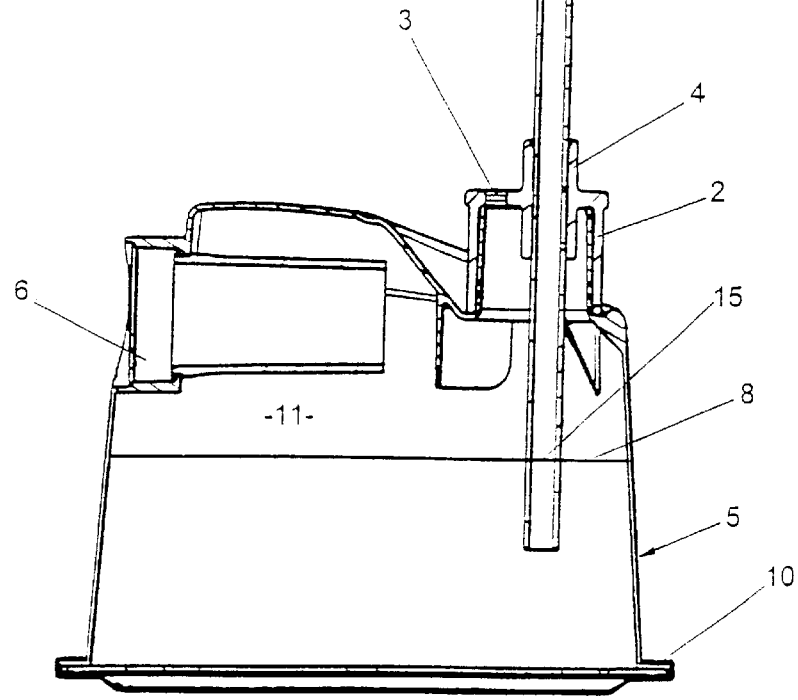
FIG. 2 is a cross sectional elevation of the chamber and measuring device as depicted in FIG. 1.
Figure 3:
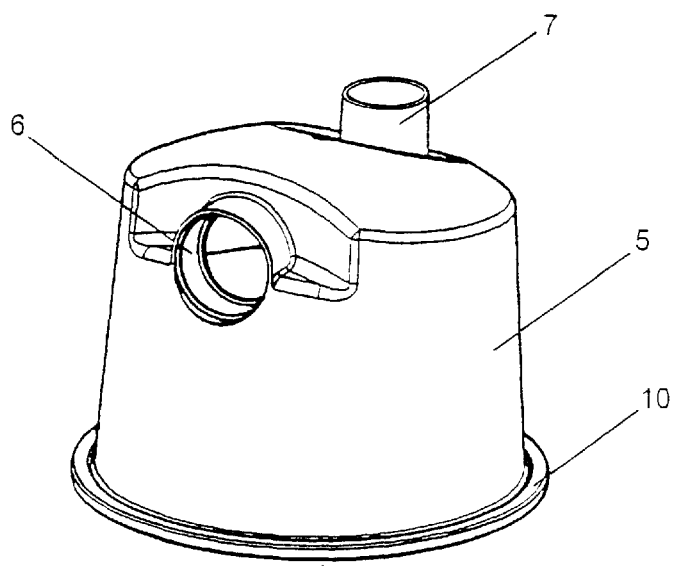
FIG. 3 is a perspective view of a humidifier chamber to which the measuring device of the present invention may be fitted.
Figure 4:
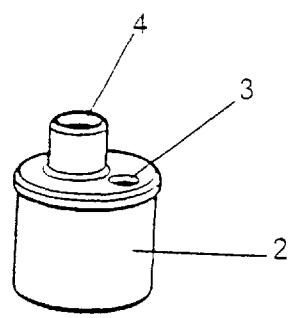
FIG. 4 is a perspective view of a connector part of the measuring device according to the present invention.
Figure 5:
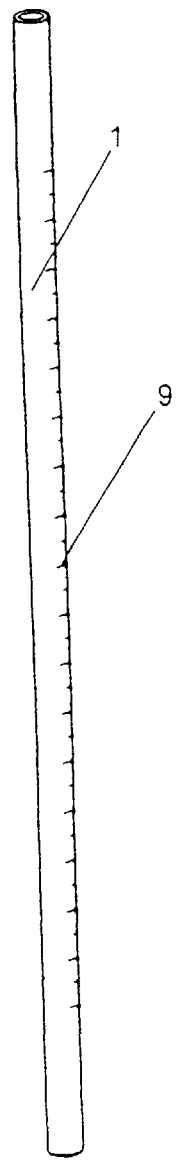
FIG. 5 is a perspective view of a calibrated tube according to the measuring device in the preferred embodiment of the present invention.

Referring to FIGS. 1–5 the preferred embodiment of the present invention is depicted with particular reference to a humidification water chamber 5 particularly adapted to connection with a CPAP blower by air blower connection port 6. The water chamber 5 has a water chamber outlet port 7.

In normal use the humidifier chamber 5 slides onto the heater base of the CPAP blower, such as the Fisher & Paykel HC200, and is retained by the peripheral flange 10. In sliding onto the heater base of the CPAP blower connection is made between the CPAP blower outlet and the air blower connection port 6. The water chamber 5 includes an annular ridge or groove 8, preferably on the inside face of the transparent chamber wall, to give an indication of the preferred maximum water level. The chamber is preferably filled to this level either before or after connection to the CPAP blower.

Once connected to the CPAP heater base the machine is activated and subsequently pressurised gases flow from the CPAP blower through air connection port 6 into the air space 11 of the chamber 5 above the reservoir of water contained therein. Simultaneously, heating of the water reservoir is provided by the heater base. Gases circulating in the air space 11 are humidified by contact with the surface of the heated water reservoir, and by the vapour leaving that surface and subsequently pass through the water chamber outlet port 7 to the user's inhalation line. The user typically receives the pressurised gases through a nasal mask. There is typically significant leakage at the nasal mask. In normal CPAP operation a continuous positive pressure is applied by the blower.

The present invention is a measuring device for measuring the output performance of the CPAP blower. The measuring device, in its preferred embodiment comprises a manometer connector 2 and manometer water column tube 1. The manometer connector 2 has a tube 4 and a bias flow outlet 3. The manometer connector is preferably formed from a soft thermoplastic material so that it can conform to and grip the outer surface of the tube 1 while allowing adjustment of the tube position and yet provided an air seal with the tube and with the water chamber outlet port.

The bias flow outlet 3 of the manometer connector 2 provides a constraint to air flow from the water chamber 5 during testing and simulates a typical flow resistance which would be experienced with a patient breathing tube, and patient that is, the resistance to flow that would typically occur in the absence of breathing. A circular hole approximately 4 mm diameter would be suitable.

The bias flow outlet could alternatively comprise a channel between the tube 1 and the tube holder 4 or between the manometer connector 2 and the water chamber outlet port 7. However, in each case the flow restriction provided by the bias flow outlet would be less accurate and therefore affect the result provided by the measuring device.

The tube holder 4 includes an annular upstanding wall to support the water column tube in a vertical orientation and allow up or down sliding action of the tube while maintaining the tube in position at least against the force of gravity. This allows the water column to be set with a zero marking 15 positioned at the level of water in the chamber 5.

The manometer water column tube 1 is preferably a cylindrical tube and for example may be formed from any suitable clear extruded thermoplastic. It is preferred that a scale 9 marked, for example, from 3 to 18 centimetres of water in 0.5 centimetres of water divisions is provided along the height of the manometer water column 1 so that an accurate blower pressure reading can be taken. Markings for example may be etched or engraved on the water column 1 or alternatively be printed on. The water column 1 also preferably includes a zero marking representing ambient or non elevated pressure from which the scale is measured, and which in use will be matched by manipulation of the water column within the holder 4 of the manometer connector 2, to the level of water in the chamber 5.

As an alternative calibration the water column 1 may include a further reference level marking representing a desired set pressure for the CPAP blower. In such case excess height above the marking indicates blower over pressure and water height lower than the marking indicates under pressure.

In normal operation the working pressure in the humidifier chamber will fluctuate between from 5 to 20 kPa above atmospheric. Accordingly the bias flow outlet is calibrated to provide a flow restriction which, in combination with the expected flow rate from the CPAP blower, gives a pressure elevation within the chamber that is within this range. For example the bias flow outlet may be sized such that in combination with the intended CPAP blower, it produces a pressure in the humidifier chamber 5–10 kPa above atmospheric.

Accordingly there will be a minimum length appropriate for the manometer water column tube 1. In particular the tube should extend to a height above the chamber water level which is in excess of the height that will be achieved by the water column in normal calibration. For example, with the conditions described above the tube should extend to a level at least 12 cm above the liquid level in the chamber.

In the use of the measuring device the water chamber 5 is filled with water to be maximum water level 8 and then connected by the air blower connection port 6 to the air blower device.

The manometer connector 2 is installed onto the water chamber outlet port 7. The manometer water column tube 1 is inserted into the water column holder 4 and adjusted to match the zero mark 15 to the water level in the water chamber 5.

The air blower device is turned on and drives the air into the water chamber 5 causing air pressure to increase causing air to flow out of the bias flow outlet 3. Air pressure in the water chamber 5 rises until air flow into the chamber matches air flow through the bias flow outlet. Air pressure in the water chamber 5 is indicated on the scale 9 of the manometer water column 1. The reference pressure provided by the CPAP blower is measured from the scale 9 of the manometer water column once stable.

While the embodiment described provides a convenient form of the invention that is readily adjustable to variations in the water chamber and the filling level thereof, it would be possible as an alternative to provide the manometer water column 1 and the manometer connector 2 as an integrated unit having fixed relative position. With the water column at a set position relative to the connector, the device would be restricted to operation with chambers having a particular distance to the surface of the water reservoir, or would be inconvenient to read as a subtraction would be required. The relative position could be set, for example, so that the effective zero level (not necessarily marked) aligned with the maximum fill line of the intended companion chamber. This however is not a preferred embodiment, it is preferred that the position of the water column tube is adjustable in the connector.

It will be readily appreciated that the present invention provides a simple and effective solution to measuring the effective output of a CPAP blower at least on a relative basis. It is therefore possible to check the correct operation of a CPAP blower or, in the case of adjustable blowers, to adjust the blower to a level corresponding to the needs of the particular user, and to subsequently test that the level is being provided.

It will also be readily appreciated that the present invention is not solely applicable to use with water chambers connected to CPAP blowers and may also be used with water chambers connected to other ventilation blowers.

What is claimed is:

1. A measuring device comprising:
   a connector formed to connect with the outlet of a humidification chamber,
   a calibrated tube extending all the way through said connector to be retained in an at least substantially vertical direction through said outlet with said connector fitted to said outlet, said calibrated tube being open at both ends and therebetween, and
   a bias flow outlet through said connector.

2. A measuring device as claimed in claim 1 wherein said bias flow outlet comprises an orifice through said connector providing a predetermined flow constraint.

3. A measuring device as claimed in claim 2 wherein said calibrated tube is slidable within said orifice through said connector.

4. A measuring device as claimed in claim 3 wherein said calibrated tube includes a visible marking at a predetermined position near the lower end thereof said lower marking for aligning with the water level in said chamber in use.

5. A measuring device as claimed in claim 4 wherein said connector has an orifice therethrough having an upstanding annular wall, and said calibrated tube has a substantially constant cross section over at least a substantial part of its length from one end thereof, said cross section providing a substantially sealed sliding fit within said orifice of said connector.

6. A measuring device as claimed in claim 2 wherein said tube includes a marking at a predetermined position closer to the upper end thereof, said upper marking indicating a desirable liquid column height in use.

7. A measuring device as claimed in claim 1 wherein said calibrated tube is slidable within an orifice through said connector.

8. A measuring device as claimed in claim 7 wherein said calibrated tube includes a visible lower marking at a predetermined position near the lower end thereof said lower marking for aligning with the water level in said chamber in use.

9. A measuring device as claimed in claim 8 wherein said tube includes a marking at a predetermined position closer to the upper end thereof, said upper marking indicating a desirable liquid column height in use.

10. A measuring device as claimed in claim 8 wherein said connector has an orifice therethrough having an upstanding annular wall, and said calibrated tube has a substantially constant cross section over at least a substantial part of its length from one end thereof, said cross section providing a substantially sealed sliding fit within said orifice of said connector.

11. A measuring device as claimed in claim 10 wherein said tube includes a marking at a predetermined position closer to the upper end thereof, said upper marking indicating a desirable liquid column height in use.

12. A measuring device as claimed in claim 7 wherein said tube includes a marking at a predetermined position closer to the upper end thereof, said upper marking indicating a desirable liquid column height in use.

13. A measuring device as claimed in claim 1 wherein said tube includes a marking at a predetermined position closer to the upper end thereof, said upper marking indicating a desirable liquid column height in use.

14. A measuring device comprising:
   a connector formed to connect with the outlet of a humidification chamber,
   a calibrated tube extending through said connector to be retained in an at least substantially vertical direction through a said outlet with said connector fitted to the said outlet and
   a bias flow outlet through said connector, said bias flow outlet comprises an orifice through said connector providing a predetermined flow constraint, said orifice is sized such that said predetermined flow constraint matches a typical flow constraint provided by a breathing circuit and patient in use.

15. A measuring device comprising:
   a connector formed to connect with the outlet of a humidification chamber,
   a calibrated tube extending through said connector to be retained in an at least substantially vertical direction through a said outlet with said connector fitted to the said outlet, and
   a bias flow outlet through said connector, said bias flow outlet comprises an orifice through said connector providing a predetermined flow constraint, said orifice being sized such that said predetermined flow constraint matches a typical flow constraint provided by a breathing circuit and patient in use,
   said calibrated tube being slidable within said orifice through said connector.

16. A measuring device as claimed in claim 15 wherein said calibrated tube includes a visible marking at a predetermined position near the lower end thereof said lower marking for aligning with the water level in said chamber in use.

17. A measuring device as claimed in claim 16 wherein said connector has an orifice therethrough having an upstanding annular wall, and said calibrated tube has a substantially constant cross section over at least a substantial part of its length from one end thereof, said cross section providing a substantially sealed sliding fit within said orifice of said connector.

18. A measuring device comprising:
   a connector formed to connect with the outlet of a humidification chamber,
   a calibrated tube extending through said connector to be retained in an at least substantially vertical direction through a said outlet with said connector fitted to the said outlet, said tube including a marking at a predetermined position closer to the upper end thereof, said upper marking indicating a desirable liquid column height in use, and
   a bias flow outlet through said connector, said bias flow outlet comprises an orifice through said connector providing a predetermined flow constraint, said orifice being sized such that said predetermined flow constraint matches a typical flow constraint provided by a breathing circuit and patient in use.

19. In a humidified gases delivery system including a humidification chamber with an outlet and a reservoir of water, a measuring device comprising:
   a connector connected with said outlet of said humidification chamber,
   a calibrated tube extending all the way through said connector to be retained in an at least substantially vertical direction through said outlet, said tube having an end in said reservoir of water, and
   a bias flow outlet through said connector.

* * * * *